United States Patent [19]

Condreva

[11] Patent Number: 5,594,250
[45] Date of Patent: Jan. 14, 1997

[54] METHOD FOR DETECTING WATER EQUIVALENT OF SNOW USING SECONDARY COSMIC GAMMA RADIATION

[76] Inventor: Kenneth J. Condreva, 1420 Fifth St., Livermore, Alameda County, Calif. 94550

[21] Appl. No.: 415,406

[22] Filed: Apr. 3, 1995

[51] Int. Cl.⁶ .................................................... G01T 1/20
[52] U.S. Cl. ................ 250/361 R; 250/362; 250/363.01; 250/357.1
[58] Field of Search .............................. 250/361 R, 362, 250/363.01, 357.1

[56] References Cited

U.S. PATENT DOCUMENTS

| | | | |
|---|---|---|---|
| 3,626,187 | 12/1971 | Laney | 250/362 |
| 3,665,180 | 5/1972 | Guillot et al. | 378/53 |
| 3,843,887 | 10/1974 | Morrison | 250/358.1 |
| 3,975,641 | 8/1976 | Morrison | 250/393 |
| 4,047,042 | 9/1977 | Wada et al. | 250/390 |
| 4,992,667 | 2/1991 | Abelentsen et al. | 250/390 |

FOREIGN PATENT DOCUMENTS 861635  1/1971  Canada ................................. 250/207

*Primary Examiner*—Michael J. Tokar
*Assistant Examiner*—Virgil O. Tyler
*Attorney, Agent, or Firm*—Timothy D. Stanley; Donald A. Nissen; Gregory A. Cone

[57] ABSTRACT

Water equivalent of accumulated snow determination by measurement of secondary background cosmic radiation attenuation by the snowpack. By measuring the attenuation of 3–10 MeV secondary gamma radiation it is possible to determine the water equivalent of snowpack. The apparatus is designed to operate remotely to determine the water equivalent of snow in areas which are difficult or hazardous to access during winter, accumulate the data as a function of time and transmit, by means of an associated telemetry system, the accumulated data back to a central data collection point for analysis. The electronic circuitry is designed so that a battery pack can be used to supply power.

11 Claims, 2 Drawing Sheets

METHOD FOR DETECTING WATER EQUIVALENT OF SNOW USING SECONDARY COSMIC GAMMA RADIATION

STATEMENT OF GOVERNMENT INTEREST

The United States Government has rights in this invention pursuant to Contract No. DE-AC04-76DP00789 between the United States Department of Energy and Sandia National Laboratories.

BACKGROUND OF THE INVENTION

The present invention relates generally to the use of cosmic radiation as a measurement tool, and more particularly, the ability to use the attenuation of cosmic gamma radiation passing through a given accumulation of snow to determine its water equivalent.

In geographic areas where the water supply is derived mainly from snow runoff, the ability to forecast accurately the snowpack water equivalent is a critical factor in the prudent allocation of water resources. Consequently, there has been a long felt need for an inexpensive, reliable and practical method for determining these data. In the United States, the annual snowpack in the Sierra Nevada, Cascade and Rocky Mountain ranges provide the bulk of the water supply for most of the western states. Also, significant parts of New England are serviced by snow runoff from the Appalachians. For these same reasons, many foreign countries are also interested in snow hydrology, including Canada, several European countries, Russia, and Japan.

In a geographic area such as California, on the slopes of the Sierra Nevada alone, there are currently four hundred snow survey sites that are monitored for snow water content to assist in annual water allocation forecasts. One hundred twenty of the sites are automated. These sites use snow pillows (a grid of four 3 foot square hydraulically suspended steel pads that weigh the snow deposited on them) connected to a weather station. The snow pillows are physically imposing and incur high installation as well as high annual maintenance costs; their size makes them very difficult to install in remote locations. The remainder of the snow survey sites require "core samples" that are taken at 2 week intervals during the snow season. As the demand on water resources increases there is a corresponding need to automate more snow survey sites in order to forecast more accurately snow runoff and allocate resources appropriately; in particular, to have more sampling sites, to automate data collection and to have the capability of recovering data as it is being generated. However, to automate these sites with current technology (e.g. snowpillows) would be expensive because of the physical size of the equipment, along with the difficulty in placing such equipment in remote locations. Because of the mountainous terrain generally encountered in establishing or maintaining current automated snow survey sites, support personnel and equipment must often be transported to remote sites by helicopter, an expensive and often hazardous activity. In spite of these dificulties, the need for these data is urgent enough to justify the expense of installation and maintenance. It is estimated that there are approximately 1300 automated snowpack sites in the United States having a total annual estimated maintenance cost in excess of one million dollars. The California State Department of Water Resources alone spends in excess of one hundred thousand dollars annually in maintenance costs for its 120 snow pillows.

In addition to the techniques described above, radioactive techniques for measuring the snow water equivalent have been reported in the literature. Smith et al. in Canadian Patent No. 861635 describes a technique that uses active sources of gamma radiation which are biologically dangerous and pose obvious environmental and safety concerns. A second technique has been described by Wada et al. in U.S. Pat. No. 4,047,042 which utilizes ground based detectors for monitoring cosmic neutron radiation. This technique suffers from accuracy limitations due to very low counting rates and interference due to soil moisture. A third technique, described by Abelentsev et al. in U.S. Pat. No. 4,992,667, utilizes fixed gamma ray detectors located above the snow-pack to monitor the variation in the natural emissions of gamma radiation from the earth (as opposed to secondary background cosmic gamma radiation) versus snow depth. Terrestrial gamma rays are low energy radiation, typically having energies less than 200 keV. As a consequence, they are rapidly attenuated by water. One measure of the attenuation of gamma rays is the e-folding depth, i.e., the depth at which the gamma ray intensity falls to 1/e. In water, terrestrial gamma rays have an e-folding depth of approximately 9 cm and thus cannot be used to monitor snowpack with a water equivalent of more than 30–40 cm. Consequently, this technique is limited to snow depths less than is typical in most mountain areas. Furthermore, because of the significant atmospheric attenuation of terrestrial gamma radiation monitoring by aircraft must be carried out at low altitudes. It cannot be used in deep mountainous terrain because of safety factors. For reasons discussed above, deep mountainous snowpacks also drastically attenuate the terrestrial gamma radiation, leading to often unreliable and inaccurate data. Because of the urgent need for these data and despite the drawbacks set forth above, water equivalent data generated from measurements of terrestrial gamma ray attenuation are used to calculate snowmelt and update forecasting models. The present invention discloses method and apparatus for determining the water equivalent of snowpack which, by measuring the attenuation of secondary cosmic gamma radiation, has significant advantages over existing techniques.

SUMMARY OF THE INVENTION

The invention disclosed herein provides a new solution to the problem of forecasting the water equivalent of snow, particularly in remote locations. Method and apparatus are described which allow the accurate measurement of the water equivalent of snowpack using apparatus which is practical and inexpensive, easy to install, requires little or no maintenance, and makes data from a remote location available in real time. The present invention fulfills these requirements and overcomes the limitations of each of the above-described existing techniques by measuring the attenuation of secondary cosmic gamma radiation rather than primary cosmic radiation, including neutrons, naturally occurring terrestrial radiation, or active radiation sources to determine the snowpack water equivalent.

Cosmic radiation is a stream of ionizing radiation of extraterrestrial origin, consisting chiefly of protons, alpha particles, and other atomic particles, including high-energy electrons, that enters the atmosphere, collides with atomic nuclei there and as a result of these collisions secondary radiation is produced, principally pions, muons, electrons and gamma radiation. Consequently, cosmic background gamma radiation can itself serve as a radiation source. Also, for a given detector volume, the cosmic gamma ray flux is about 100 times that for cosmic neutrons. There is no interference due to soil composition because the energy range utilized by this method is greater than that of any terrestrial source of gamma radiation. Because of their higher energy, the secondary cosmic gamma rays employed for the purposes of this invention have a much deeper penetration in water than terrestrial gamma rays. The energy range used for this invention ranges from about 3 MeV to 10 MeV; the e-folding depth in water is about 66 cm for 10 MeV gamma rays.

The invention described herein is directed to a method of remotely determining the water equivalent of a given accumulation of snow. Accordingly, it is an object of this invention to use the attenuation of secondary background cosmic gamma radiation by snow to determine the water equivalent of snowpack. Another object of this invention is to perform this measurement remotely and transmit the data in real time.

This invention can be implemented with a gamma ray detector such as a scintillator type radiation detector. The scintillator and its associated instrumentation may be located at the soil surface. As snow accumulates over time, the snowpack water equivalent is determined by monitoring the decrease in secondary background cosmic gamma radiation intensity as the snowpack increases. Where a scintillation type radiation detector is used to detect gamma rays, a photodetection system and a pulse height analyzer are used to count gamma rays penetrating through the snowpack to the detector. A power supply coupled with a telemetry system for transmitting data from remote locations completes the instrument package. Because variations in flux of cosmic radiation throughout the year can lead to errors in the determination of the water equivalent another embodiment of this invention employs a second detector positioned above the snowpack to record these variations. The data received from the second detector may then be used to correct attenuation data. In another embodiment of this invention, a second scintillator of similar size can be placed directly below and contiguous with the primary detector to allow anticoincident exclusion of false readings due to the high energy primary cosmic radiation. The inventor has determined that while secondary cosmic rays generally could be employed to perform the measurements described herein, there is a preferable energy range that is desired. The preferred energy range, from 3 to 10 MeV, is high enough to measure snow accumulations that could reasonably be expected to be encountered but low enough to make the detector size of practical dimensions.

The objects of the present invention together with additional objects, novel features and advantages thereof over existing prior art forms, which will become apparent to those skilled in the art from detailed disclosure of the present invention as set forth hereinbelow, are accomplished by the improvements herein described and claimed.

BRIEF DESCRIPTION OF THE DRAWINGS

The accompanying drawings, which are incorporated in and form part of the specification, illustrate the present invention and, together with the description, explain the invention.

DESCRIPTION OF THE INVENTION

The method of measuring the water equivalence of snowpack as set forth in this invention is based on a relative measurement of the attenuation of secondary cosmic gamma radiation by the water present in snow.

Snow is comprised almost entirely of water and air and the attenuation characteristics for gamma rays of both water and air at a gamma ray energy of 5 MeV are shown in Table 1. These data clearly indicate that water will attenuate gamma radiation and that the attenuation of gamma radiation by air is insignificant compared to that of water. Therefore, the gamma ray attenuation of snow that is measured is due almost exclusively to the water content of the snow.

TABLE 1

| Gamma Ray Attenuation Characteristics of Water and Air at 5 MeV | | |
|---|---|---|
| | Air | Water |
| Mass Absorption Coeff. ($cm^2/g$) | 0.0180 | 0.0195 |
| Material Density ($g/cm^3$) | 0.00138 | 1.00 |
| e-folding attenuation depth (cm) | 40257.6 | 51.28 |

Because the present invention employs a relative measurement of the attenuation of cosmic gamma rays to determine the water equivalent of snow it is first necessary to determine the attenuation characteristic for water by measuring the decrease in secondary background cosmic radiation as it passes through water samples of varying but known depths; in this case, for radiation between 3 to 10 MeV. The resulting experimental data measures, determines and calibrates the attenuation characteristic of water. In the field, a measure of secondary background cosmic gamma radiation incident upon a given area is first obtained. As the snowpack increases, the decrease, or attenuation, in secondary background cosmic gamma radiation for that area is measured. The snowpack water equivalent is then obtained by comparing the attenuation of secondary gamma radiation caused by snowpack water with calibration data relating gamma ray attenuation with water content.

Figure 1:
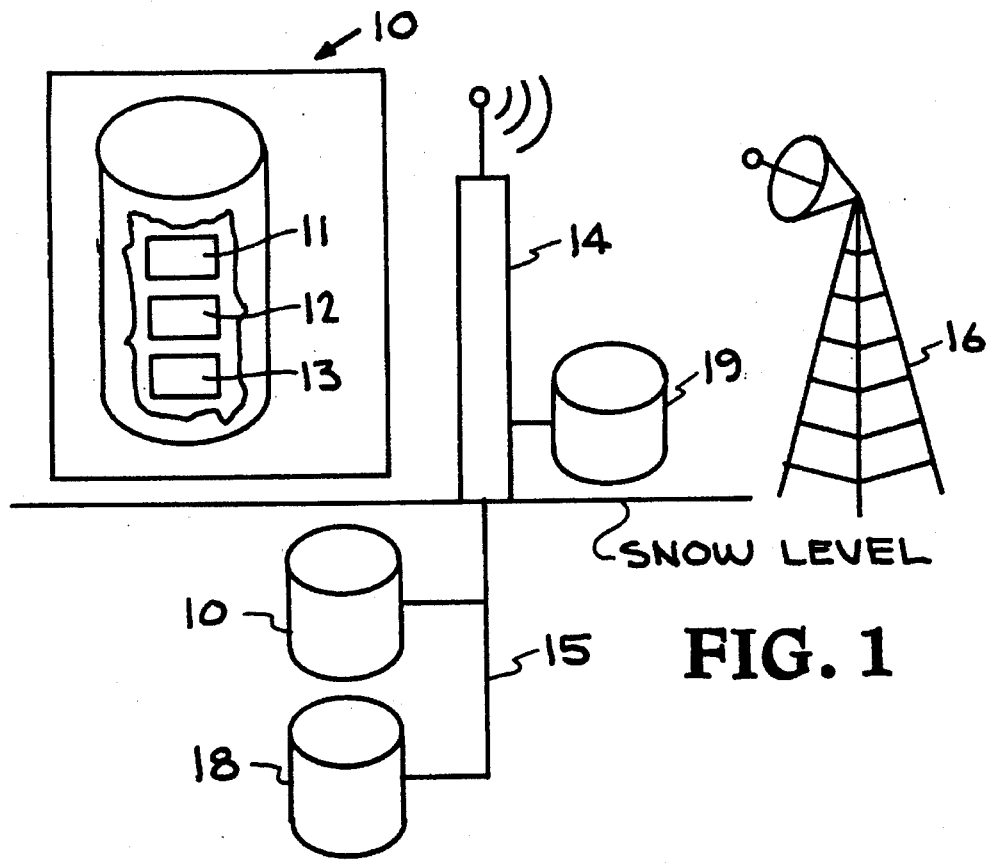
FIG. 1 is a diagram showing an arrangement of equipment used to measure attenuation of cosmic gamma rays by snow.
Figure 4:
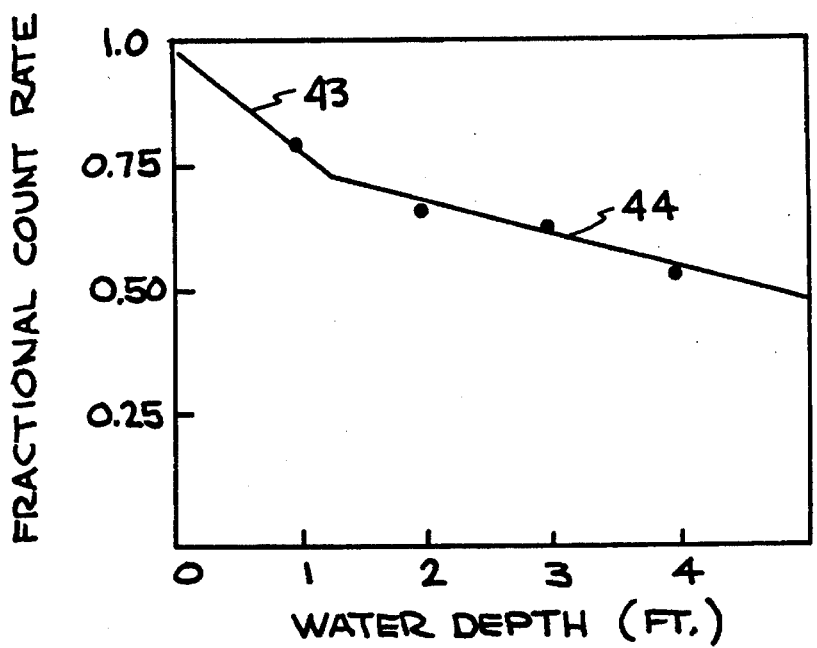
FIG. 4 shows the fractional count rate of background gamma radiation in the 2.7 MeV to 8 MeV range vs. depth in water using a 2 inch NaI scintillator detector.

A cosmic gamma ray measurement and data transmission system suitable for determining snow water equivalency at the site of interest is depicted in FIG. 1. It may consist of a ground level unit 10 containing a gamma ray detector 11, a printed wiring board holding electronic circuitry for converting signals from the gamma ray detector 12 into electrical pulses suitable for counting, counting those pulses that fall within a specified energy range and accumulating said counts for later use and a power supply 13. A transmission antenna 14 may be installed on a pole or some structure at a height exceeding the anticipated maximum snow depth. The ground unit may be connected to the antenna via a coaxial cable 15 thus allowing periodic radio frequency transmission of the gamma ray count rate data at various time intervals to a central data receiving station 16. The data generated by this ground level unit could then be compared to data obtained from "above the snowpack" reference unit 19 to obtain snow water equivalency at each site by computing fractional count rate data similar to that shown in FIG. 4. Because variations in flux of cosmic radiation throughout the year can lead to errors in the determination of the water equivalent another embodiment of this invention employs a second detector 19 positioned above the snowpack to record these variations. The data received from the second detector 19 can then be used to correct attenuation data. In another embodiment of this invention, a second detector of similar size 18 can be placed directly below and contiguous with primary detector 15 to allow anticoincident exclusion of false readings due to the high energy primary cosmic radiation.

Figure 2:
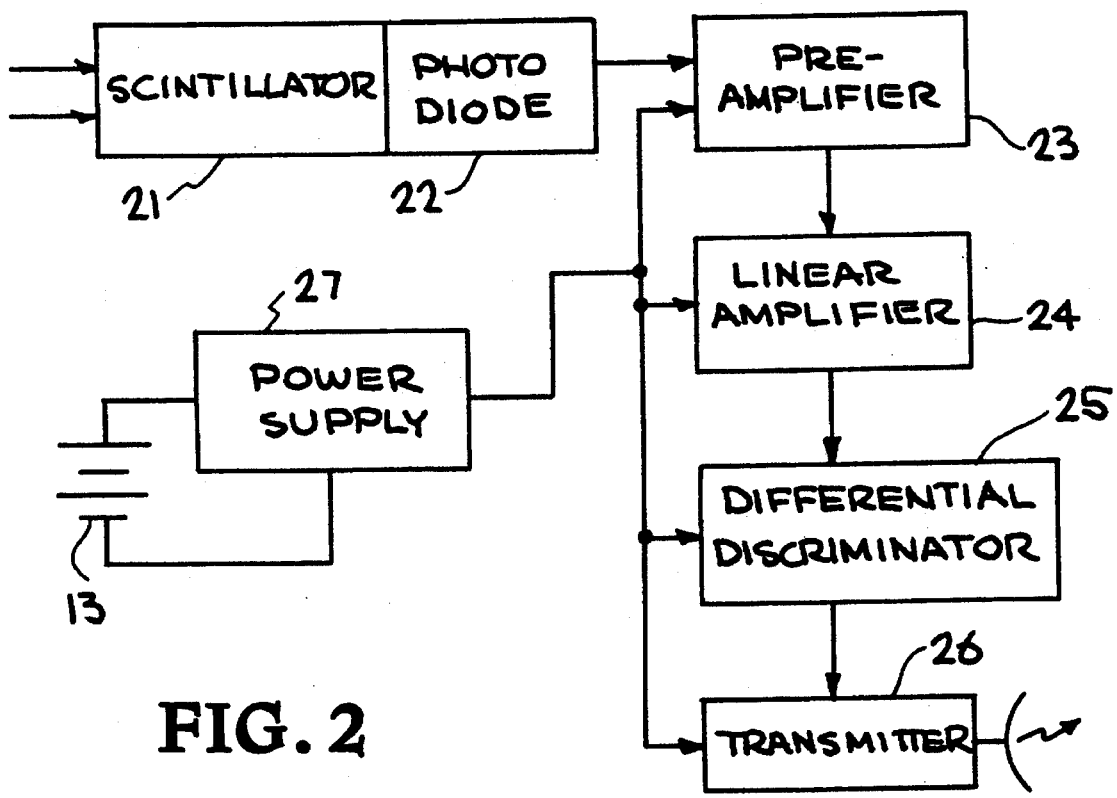
FIG. 2 is a block diagram of a cosmic ray measurement system suitable for field use in determining the water equivalent of snowpack.

FIG. 2 shows a block diagram of a cosmic gamma ray detection system, suitable for use in the field. The unit may consist of a large diameter (3 inch or more) CsI(Tl) scintillator 21, a photodetector 22 (a large area photodiode), a miniaturized electronics subsystem containing a preamplifier 23, a linear amplifier 24, a differential discriminator circuit 25 that counts pulses only within a specific peak voltage corresponding to the gamma ray energy range of interest, a telemetry transmitter 26, and a battery pack 13 to provide power 27 to the electronics.

Figure 3:
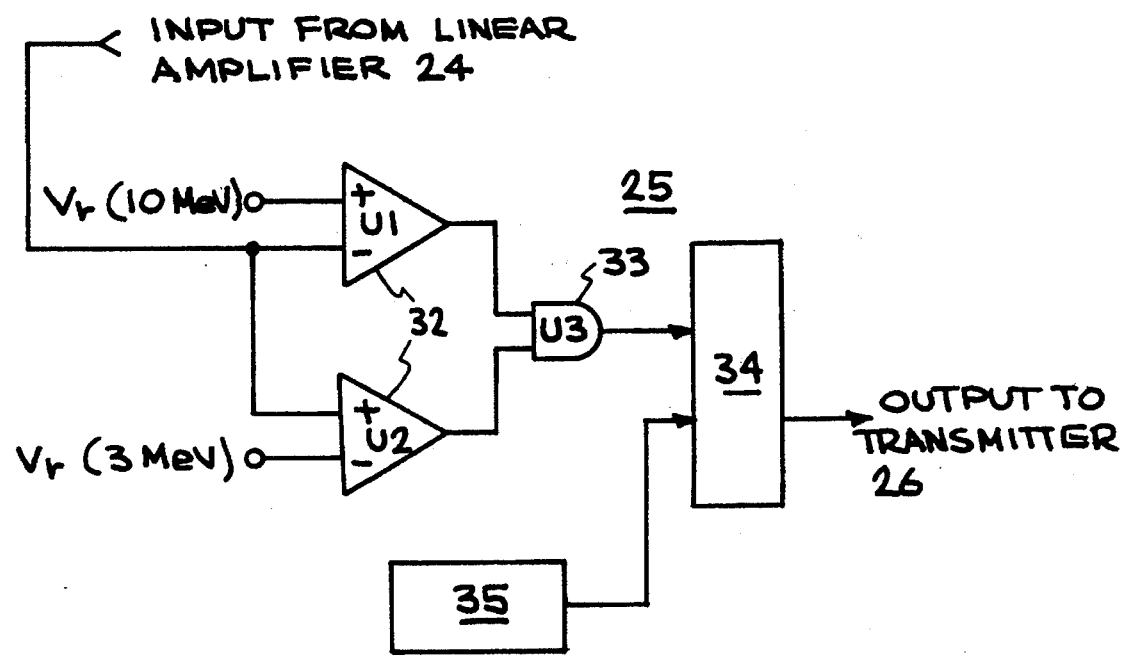
FIG. 3 is a diagram of the differential discriminator portion of the cosmic gamma ray measurement system.

A more detailed diagram of the differential discriminator unit 25 is depicted in FIG. 3. In this figure, a window comparator circuit 32 comprising (voltage comparators 36 and 37) receives as an input the signal from the linear amplifier 24 and distinguishes pulses corresponding to the gamma energy range of interest (3 MeV to 10 MeV). When the signal is within the desired range (output of AND gate 33 is high), the system controller 34 receives a pulse. Pulses are accumulated for a time interval determined by the Period Timer circuit 35. The total counts for each time period are then formatted by the system controller and converted to a serial data stream suitable for modulation of the radio frequency (r.f.) transmitter. This electronics system, due to its small size and low power requirements, would be suitable for remote, battery operated application as described by this invention.

The experiment described hereinbelow was performed to determine the attenuation characteristic of secondary cosmic gamma rays by a column of water. This expriment illustrates the present invention and the attenuation data derived therefrom may be used as calibration data to determine the water equivalent of snowpack A two inch NaI scintillation detector and photodetector array similar to that shown in FIG. 2 (21&22) was lowered to various depths into a pool of water. The total gamma ray count over the energy range of 2.7 MeV to 8 MeV was recorded for several hours at various depths and compared to the count rate at the surface of the water. This energy range was selected for this experiment because energies below 2.7 MeV would include undesired counts from terrestrial background gamma sources, and 8 MeV was the upper detection limit of the particular scintillator used in the experiment. The resulting data, which was recorded using a portable multichannel analyzer, is shown graphically in FIG. 4 which depicts a measure of fractional count rate versus water depth. As was expected a dual slope was observed in FIG. 4. The initial slope 43 observed in the plot for water depths up to approximately 2 feet is the anticipated gamma attenuation. The more gradual slope 44 at larger depths was indicative of the detection of high energy particles of primary cosmic radiation (e.g. protons, μ-mesons). The primary radiation could be accounted for by an anticoincident detection scheme using two scintillators, or, the deeper penetration of the particles of primary gamma radiation could be exploited for measurement of extreme water depths, usually greater than 5 feet.

Although a preferred embodiment of the present invention has been described, the spirit and scope of the invention is by no means restricted to what is described above. For example, within the general framework of the description given above, another type of gamma ray detector may be substituted for the preferred Cs(Tl) scintillator, as long as such a detector accomplishes the general purpose of detecting secondary cosmic background gamma radiation.

I claim:

1. A method for determining the water equivalent of an accumulation of snow, comprising:
    a) obtaining a measurement of a first flux of secondary cosmic gamma rays which has passed through an accumulation of snow; and
    b) comparing said measurement with calibration data to determine the water equivalent of said accumulation of snow.

2. The method of claim 1 further including measuring a second flux of secondary gamma radiation incident upon said accumulation, comparing the measurements of said first and second gamma ray fluxes to determine the attenuation of said cosmic gamma radiation by said accumulation.

3. An apparatus for determining the water equivalent of an accumulation of snow comprising:
    a) a scintillation detector located at the bottom of an accumulation of snow, said scintillation detector generating a light pulse when struck by a gamma ray;
    b) a photodetector to detect said light pulse and convert said light pulse to an electrical pulse;
    c) an electronics system receiving said electrical pulse, comprising;
        i) at least one amplifier to amplify said electrical pulse to a magnitude useful for a differential discriminator;
        ii) a differential discriminator for counting said pulse whenever said pulse falls within a range of from about 3 to about 10 MeV, accumulating pulses that fall within said range for a time interval, and formatting the accumulated pulses into a serial data stream suitable for transmission;
    d) a period timer circuit for determining the time interval over which pulses are accumulated;
    e) a telemetry transmitter for transmitting accumulated pulses; and
    f) a power supply for powering the electronics system.

4. The method of claim 1, further including obtaining a measurement of secondary cosmic gamma radiation having an energy level of at least 3 MeV.

5. The method of claim 1, further including obtaining a measurement of secondary gamma radiation having an energy level no greater than 10 MeV.

6. The method of claim 1 further including obtaining a second measurement of the first flux of the secondary cosmic gamma rays for anticoincidence exclusion of false readings.

7. An apparatus for determining the water equivalent of an accumulation of snow, comprising:
    a) first means for detecting a first flux of secondary cosmic radiation which has passed through an accumulation of snow; and
    b) means for determining the water equivalent of said snow accumulation from said first flux of secondary cosmic radiation.

8. The apparatus of claim 7, further including means for counting secondary cosmic gamma radiation within an energy range of from about 3 to about 10 MeV.

9. The apparatus of claim 7, further including means for transmitting gamma radiation counts to a data collection point.

10. The apparatus of claim 7, further including:
- second means for detecting the flux of secondary cosmic gamma radiation incident upon the accumulation of snow; and
- means for correcting the first flux of secondary cosmic gamma radiation for variations in the incident cosmic gamma radiation.

11. The apparatus of claim 7, further including:
- third means for detecting the first flux of secondary cosmic gamma radiation; and
- means for anticoincidence exclusion of false readings due to high energy primary cosmic radiation detected by said first detection means.

\* \* \* \* \*